United States Patent [19]
Sugiya et al.

[11] Patent Number: 5,663,419
[45] Date of Patent: Sep. 2, 1997

[54] BIFUNCTIONAL ALKYL PHOSPHINE OXIDE AND PRODUCTION METHOD THEREOF

[75] Inventors: Masashi Sugiya; Tsutomu Watanabe; Seiji Shimura, all of Tokyo, Japan

[73] Assignee: Nippon Chemical Industrial Co., Ltd., Tokyo, Japan

[21] Appl. No.: 628,511

[22] Filed: Apr. 5, 1996

[51] Int. Cl.$^6$ .................................................. C07F 9/53
[52] U.S. Cl. .................................. 560/190; 562/594
[58] Field of Search ............................ 560/190, 195; 562/594

[56] References Cited

U.S. PATENT DOCUMENTS 4,537,993  8/1985  Savides et al. ............................ 568/14

FOREIGN PATENT DOCUMENTS

| 0 156 139 | 10/1985 | European Pat. Off. . |
| 6-166693 | 6/1994 | Japan . |
| 6-166692 | 6/1994 | Japan . |

OTHER PUBLICATIONS

Database CAPLUS on STN, Columbus: Chemical Abstracts Service, Acc. No. 1995:312301, Japan Kokai No. 06–166692, abstract 1995.

Database CAPLUS on STN, Columbus: Chemical Abstracts Service, Acc. No. 1995:312302, Japan Kokai No. 06–166693, abstract 1995.

*Primary Examiner*—Johann Richter
*Assistant Examiner*—Michael G. Ambrose
*Attorney, Agent, or Firm*—Oblon, Spivak, McClelland, Maier & Neustadt, P.C.

[57] ABSTRACT

A bifunctional alkyl phosphine oxide which is represented by the following general formula (1),

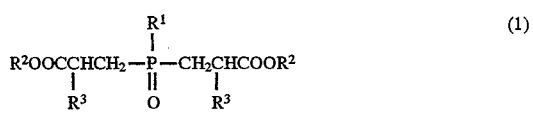

wherein $R^1$ represents tert-butyl or 1,1,3,3-tetramethylbutyl, and a production method thereof. This organophosphorus compound is useful a wide variety of fields including a flame retardant, antistatic additive, antibacterial agent, dyeing-improving agent, resin modifier, stain-proofing agent, and rust preventives. This compound can be produced industrially advantageously.

11 Claims, No Drawings

BIFUNCTIONAL ALKYL PHOSPHINE OXIDE AND PRODUCTION METHOD THEREOF

BACKGROUND OF THE INVENTION

The present invention relates to a new bifunctional alkyl phosphine oxide and a production method thereof. In particular, the present invention relates to a new bifunctional alkyl phosphine oxide which is useful for imparting flame retardant properties and antistatic properties and the like to fibers, plastics and the like.

Fibers, plastics and the like are required to have high functionality such as flame retardant properties, resin modifying properties, and antistatic properties. Bis(carboxyethyl) methyl phosphine oxide derived from an organophosphorus compound such as methyl phosphine has been used for these purposes. It is disclosed in U.S. Pat. No. 4,127,566 that polyesters wherein this compound is co-polymerized show good flame retardant properties. This polyester copolymer, however, has such drawbacks as a markedly lowered melting point and a somewhat low heat resistance.

In addition, methyl phosphine, which is to be used as a raw material, is in gaseous form at ordinary temperatures and under ordinary pressures, and can thus easily ignite and explode when contacted with air. Therefore, it is a very dangerous and hard-to handle substance. Moreover, it also is highly toxic, as well. Accordingly, it is desired that a monoalkyl phosphine which can be easily handled and which has low toxicity be provided.

Recently a method of producing a phosphine oxide represented by the general formula (5) which is used as a raw material monomer for a flame-resistant polyester copolymer has been disclosed (Japanese Patent Laid-Open Hei 6-166692, Japanese Patent Laid-Open Hei 6-166693),

wherein, L represents an alkyl group, aryl group, aralkyl group, or a saturated alicyclic compound, M represents a hydrogen atom or an alkyl group having 1 to 4 carbon atoms, and N represents a hydrogen atom or methyl group.

According to the above-mentioned production method, the phosphine oxide is synthesized by reacting a primary phosphine and acrylonitrile, carrying out purification by distillation, followed by oxidation with hydrogen peroxide and hydrolysis with an alkali, or it is synthesized in a different order, that is, by carrying out the hydrolysis with an alkali, followed by oxidation with hydrogen peroxide. These methods, however, have such drawbacks that the synthesis requires a long process, and it is difficult to separate the product from the ammonium chloride which is generated in large amounts as a by-product during the hydrolysis. Thus, a product of high purity is hard to obtain. Though the publication discloses a compound of formula (5) wherein L is butyl, this compound is not described in the examples. As a matter of fact, the compound wherein L is t-butyl or 1,1,3,3-tetramethylbutyl cannot be produced in a method similar to the above-mentioned prior art technique (see following Comparative Example 1). The monophenyl phosphine disclosed in the example as an illustrative example of the primary phosphine, is hard to obtain, and the price is high.

In addition, illustrative compounds and synthesis methods according to the present invention are not disclosed at all in the publications.

In view of the above-mentioned facts, the present inventors carried out an intensive study of a bifunctional alkyl phosphine oxide as the functional organophosphorus compound, and identified a new bifunctional alkyl phosphine oxide.

The present inventors also found that a new bifunctional alkyl phosphine oxide of high purity can be produced in high yields, by carrying out reaction of a monoalkyl phosphine with (meth)acrylic acid or an ester thereof in the presence of an acid catalyst, and by adding an oxidizing agent to the resulting mixture to carry out the reaction, to thereby complete the present invention.

SUMMARY OF THE INVENTION

Accordingly an object of the present invention is to provided a bifunctional alkyl phosphine oxide represented by the following general formula (1),

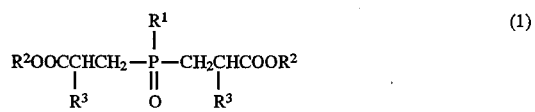

wherein $R^1$ is an alkyl group represented by the following general formula (2),

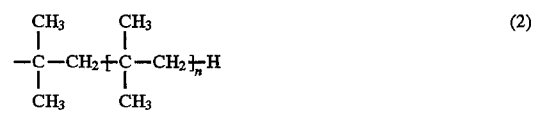

wherein n represents an integer of 0 to 1, $R^2$ represents a hydrogen atom, an alkyl group and a hydroxyalkyl group having 1 to 8 carbon atoms, and $R^3$ represents a hydrogen atom and methyl group.

Another object of the present invention is to provide a method of producing a bifunctional alkyl phosphine oxide according to claim 1, wherein a monoalkyl phosphine represented by the following general formula (3),

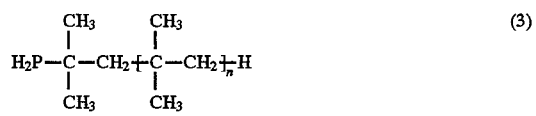

wherein n represents an integer of 0 to 1, is allowed to react with (meth) acrylic acid or an ester thereof (hereinafter referred to as "acrylic ester and the like") represented by the following general formula (4),

wherein $R^2$ represents a hydrogen atom, an alkyl group and a hydroxyalkyl group having 1 to 8 carbon atoms, and $R^3$ represents a hydrogen atom or methyl group, in the presence of an acid catalyst, and then an oxidizing agent is added to the reaction mixture to carry out the reaction.

According to the present invention, there is provided a bifunctional alkyl phosphine oxide and a production method thereof. The bifunctional alkyl phosphine oxide is useful for imparting flame retardant properties, antistatic properties and the like to fibers or plastics. The bifunctional alkyl phosphine oxide of high selectivity and high purity can be advantageously produced industrially by reacting a monoalkyl phosphine with a (meth) acrylic ester in the presence of an acid catalyst, followed by adding an oxidizing agent to the solution to carry out reaction.

This organophosphorus compound has been used in a wide variety of fields including use as a flame retardant, antistatic additive, antibacterial agent, dyeing improving agent, resin modifier, stain-proofing agent, and rust preventive.

DETAILED DESCRIPTION OF THE INVENTION

The present invention will now be described in detail.

(A compound according to the present invention)

The compound of general formula (1) which is a bifunctional alkyl phosphine oxide according to the present invention, is a new compound.

Illustrative examples of the compound according to the present invention include bis-(2-carboxyethyl)-1,1,3,3-tetramethylbutylphosphine oxide, bis-(2-carbethoxyethyl)-1,1,3,3-tetramethylbutylphosphine oxide, bis[2-carbo(2-hydroxyethoxy)ethyl]-1,1,3,3-tetramethylbutylphosphine oxide, bis(2-carboxypropyl)-1,1,3,3-tetramethylbutylphosphine oxide, bis-(2-carboxyethyl)-tert-butylphosphine oxide, bis-(2-carbethoxyethyl)-tert-butylphosphine oxide, bis-[2-carbo(2-hydroxyethoxy)ethyl]-tert-butylphosphine oxide, bis-(2-carboxypropyl)-tert-butylphosphine oxide and the like.

As the above-mentioned general formula (1) shows, the phosphorus-containing compound of the present invention has two carboxyl groups. Thus it is bifunctional, and exhibits polymerizability for both homopolymerization and copolymerization with another monomer.

Also, this compound exhibits remarkably superior chemical and thermal stabilities, in comparison with other organophosphorus compounds having a P—O bond, since it has a P—C bond between the carbon atom and the phosphorus atom in the functional group.

In the compound according to the present invention, $R^1$ in the general formula (1) is an alkyl group having a branched structure, particularly, t-butyl, or 1,1,3,3-tetramethylbutyl.

When a compound of the present invention, having a bulky substituent such as a branched alkyl group, is co-polymerized in polyesters and the like, the resulting polyester and the like exhibit an elevated conversion temperature as well as heat resistance to a higher temperature, due to increased hindrance of the internal rotation of the polymer. The compound of the present invention is generally a white crystal or a colorless and transparent liquid at ordinary temperature, depending on the types of $R^1$, $R^2$ and $R^3$ in the above-mentioned general formula (1). An ester type in which $R^2$ is an alkyl having 1 to 4 carbon atoms is particularly useful from economic and industrial points of view.

(Method of producing the compound of the present invention)

The bifunctional alkyl phosphine oxide of the present invention can be produced by carrying out reaction of a monoalkyl phosphine represented by the following general formula (3),

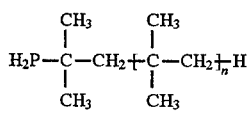   (3)

wherein n represents an integer of 0 to 1, with a (meth) acrylic ester and the like represented by the following general formula (4),

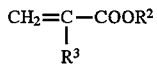   (4)

wherein $R^2$ represents a hydrogen atom, an alkyl group and a hydroxyalkyl group having 1 to 8 carbon atoms, and $R^3$ represents a hydrogen atom or methyl group, in the presence of an acid catalyst, followed by adding an oxidizing agent to the reaction mixture and carrying out the reaction.

(Monoalkyl phosphine)

The monoalkyl phosphine used as a raw material for producing the bifunctional alkyl phosphine oxide according to the present invention can be represented by the general formula (3), and illustrative examples include 1,1,3,3-tetramethylbutyl-phosphine, and tert-butylphosphine.

(Acrylic ester and the like)

As a (meth)acrylic ester and the like used as another raw material, any compound can be used as long as it can be represented by the formula (4), and illustrative examples include acrylic acid, acrylic acid methyl ester, acrylic acid ethyl ester, acrylic acid butyl ester, acrylic acid 2-ethyl hexyl ester, methacrylic acid, methacrylic acid methyl ester, methacrylic acid ethyl ester, methacrylic acid butyl ester, methacrylic acid 2-ethyl hexyl ester, acrylic acid 2-hydroxy ethyl ester and the like.

(Acid catalyst)

The reaction between the above-mentioned two compounds proceeds in the presence of an acid catalyst. Illustrative examples of the acid catalyst to be used include proton acids such as hydrochloric acid, sulfuric acid, nitric acid, phosphoric acid, perchloric acid, periodic acid, hydrofluoric acid, and methansulfonic acid. Hydrochloric acid is particularly advantageous industrially.

(Oxidizing agent)

Illustrative examples of an oxidizing agent to be used in the subsequent step include peroxides such as hydrogen peroxide and benzoyl peroxide, nitric acid, nitrogen oxides such as NO, $N_2O_4$, and $N_2O$, and chlorine. Hydrogen peroxide is industrially advantageous.

(Reaction conditions)

As mentioned before, the reaction is carried out in two steps; the first step comprises coupling a monoalkyl phosphine with an acrylic ester and the like, and the second step comprises oxidation of the reaction product obtained in the first step. The conditions for the coupling reaction of the first step differ according to the physical properties of the starting materials, the acid catalyst and so on, however, in many cases, a small excess of an acrylic ester and the like is appropriately used, i.e. 2 to 5 moles, preferably 2 to 3 moles of the acrylic ester and the like is used for 1 mole of the monoalkyl phosphine.

As for the acid catalyst, the appropriate amount varies according to the type of catalyst and the reaction conditions, however, in most cases, 1 to 5 moles, preferably 1 to 2 moles of the acid catalyst is appropriately used for 1 mole of the monoalkyl phosphine.

The reaction temperature is $-30°$ to $30°$ C., preferably $10°$ to $20°$ C., and the reaction time is 0.5 to 24 hours, preferably 0.5 to 10 hours with stirring.

Referring now to the reaction procedure, the reaction vessel is sufficiently purged with an inactive gas such as nitrogen or helium, then in most cases after the monoalkyl phosphine and acid are added to the reactor, the acrylic ester or the like is added thereto dropwise to carry out reaction. After the reaction is completed, the reaction mixture is concentrated if necessary, and the acid catalyst is removed.

In the second step of the reaction to oxidize the reaction product of the first step, water, an alcohol or a mixture thereof is added, if necessary, to the reaction mixture obtained in the first step and an oxidizing agent is added thereto dropwise.

The appropriate amount of oxidizing agent depends on the oxidizing agent selected, however, 1.0 to 1.1 moles, preferably 1 to 1.05 moles of the oxidizing agent is appropriate for 1 mole of the initially added monoalkyl phosphine. Water, an alcohol or a mixture thereof can be added if necessary, and the amount is not particularly limited. Referring to the alcohol, an alcohol corresponding to the alkyl ester group of acrylic ester and the like is preferable, for example, methanol is preferable for acrylic acid methyl ester and ethanol is preferable for acrylic acid ethyl ester.

As for the reaction temperature, the dropping reaction is carried out at room temperature to 90° C., preferably 60° to 70° C., and subsequently maturation reaction is carried out at the same temperature for 0.5 to 10 hours, preferably 1 to 2 hours.

As for the reaction procedure, water or an alcohol is added, if necessary, to the reaction mixture obtained in the first reaction, then an oxidizing agent is added thereto dropwise with stirring to carry out reaction. After completion of the reaction, the reaction mixture is concentrated to give the bifunctional alkyl phosphine oxide of the present invention in the form of a white crystal or a colorless and transparent liquid.

According to the reaction of the present invention, in the first step, a compound of formula (3) is reacted with a compound of formula (4) in the presence of an acid catalyst to provide a tertiary phosphine hydrochloride of the following general formula (6),

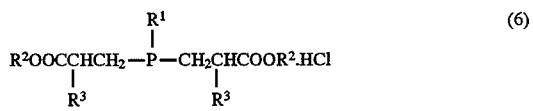

(6)

wherein $R^1$, $R^2$ and $R^3$ have the same meanings as defined above.

Then, in the second step, the tertiary phosphine hydrochloride of general formula (6) is oxidized with an oxidizing agent to give a bifunctional alkyl phosphine oxide of general formula (1).

[EXAMPLES]

To further illustrate the present invention, the following examples are given.

Example 1

A 500 ml four-neck flask equipped with a condenser, a thermometer, and a stirrer was sufficiently purged with nitrogen, and 109.7 g (0.75 mole) of (1,1,3,3-tetramethylbutyl) phosphine and 105.7 g (1.125 moles) of concentrated hydrochloric acid were charged therein under a nitrogen gas stream. 108.0 g (1.5 moles) of acrylic acid was added thereto slowly dropwise with stirring while the temperature was kept at 30° C. or less. The reaction mixture became a homogeneous, colorless and transparent liquid. The liquid was concentrated by an evaporator and the excess hydrochloric acid and water were removed.

The resulting product was dissolved in 100 ml of water and 87.6 g (0.77 mole) of 30% hydrogen peroxide was added thereto dropwise while the temperature was kept at 60° to 70° C. After completion of the dropping, the mixture was matured at 90° for 1 hour. The mixture was slowly cooled, with precipitation of a crystal starting at around 50° C. Concentration of the solution was continued until it reached to one-half of its original volume. The precipitated crystal was filtered out and washed with water, then dried in vacuum to give 202.1 g (0.66 mole) of a white crystal.

The product had a melting point of 142° C. and was identified as bis(2-carboxyethyl)-1,1,3,3-tetramethylbutylphosphine oxide by analysis with FAB-MASS, $^1$H-NMR, and FT-IR.

FAB-MASS: m/z=307[M+H]$^+$ $^1$H-NMR (CDCl$_3$, δ): 1.08 (s, 9H), 1.37 (d, 6H, J=17.3 Hz), 1.65 (d, 2H, J=8.93 Hz), 2.18 (m,4H), 2.72 (m, 4H), 8.48 (s, 2H).

The results of FT-IR analysis are shown in Table 1.

Example 2

An apparatus analogous to that of Example 1 was used and 73.1 g (0.5 mole) of 1,1,3,3-tetramethylbutylphosphine and 70.5 g (0.75 mole) of concentrated hydrochloric acid were charged therein under a nitrogen gas stream. 100.1 g (1.0 mole) of ethyl acrylate was added thereto dropwise with stirring while the temperature was kept at 30° C. or less. The reaction mixture was reacted at room temperature for 20 hours to give a homogeneous, colorless and transparent liquid. The liquid was concentrated by an evaporator and the excess hydrochloric acid and water were removed.

The resulting product was dissolved in 100 ml of ethanol and 58.9 g (0.52 mole) of 30% hydrogen peroxide was added thereto dropwise while the temperature was kept at 60° to 70° C. After completion of the dropping, the mixture was matured at 90° C. for 1 hour. The solvent and the like were removed from the reaction mixture by evaporator to give 137.7 g (0.38 mole) of a colorless, transparent and viscous liquid.

The product was identified as bis(2-carbethoxyethyl)-1,1,3,3-tetramethylbutylphosphine oxide by analysis with FAB-MASS, $^1$H-NMR and FT-IR.

FAB-MASS: m/z=363 [M+H]$^+$ $^1$H-NMR (CDCl$_3$, δ): 1.06 (s, 9H), 1.29 (t, 6H, J=7.44 Hz), 1.41 (d, 6H, J=17.3 Hz), 2.29 (m, 4H), 2.77 (m, 4H), 4.19 (q, 4H, J=7.14 Hz).

The results of FT-IR analysis are shown in Table 1.

Example 3

An apparatus analogous to that of Example 1 was used and 73.1 g (0.5 mole) of 1,1,3,3-tetramethylbutylphosphine and 70.5 g (0.75 mole) of concentrated hydrochloric acid were charged therein under a nitrogen gas stream. 116.1 g (1.0 mole) of acrylic acid 2-hydroxyethyl ester was added thereto dropwise with stirring while the temperature was kept at 30° C. or less, and reaction was carried out at room temperature for 10 hours to give a homogeneous, colorless and transparent liquid. The liquid was concentrated by an evaporator and the excess hydrochloric acid and water were removed.

The product was dissolved in 100 ml of water and 58.9 g (0.52 mole) of 30% hydrogen peroxide was added thereto dropwise while the temperature was kept at room temperature. The solvent and the like were removed from the reaction mixture by an evaporator to give 161.7 g (0.41 mole) of a colorless and transparent viscous liquid.

The product was identified as bis-[2-carbo(2-hydroxyethoxy)ethyl]-1,1,3,3-tetramethylbutylphosphine oxide by analysis with FAB-MASS, $^1$H-NMR and FT-IR.

FAB-MASS: m/z=395[M+H]$^+$ $^1$H-NMR (CDCl$_3$, δ): 1.06 (s, 9H), 1.36 (d, 6H, J=17.3 Hz), 1.53 (d, 2H, J=8.33 Hz), 2.13 (m, 4H), 2.77 (m, 4H), 3.70 (s, 2H), 3.80 (m, 4H), 4.30 (m, 4H).

The results of FT-IR analysis are shown in Table 1.

Example 4

An apparatus analogous to that of Example 1 was used and 73.1 g (0.5 mole) of 1,1,3,3-tetramethylbutylphosphine and 70.5 g (0.75 mole) of concentrated hydrochloric acid were charged therein under a nitrogen gas stream. 86.1 (1.0 mole) of methacrylic acid was added thereto dropwise with stirring while the temperature was kept at 30° C. or less, and reaction was carried out at room temperature for 5 hours to give a homogeneous, colorless and transparent liquid. The liquid was concentrated by an evaporator and the excess hydrochloric acid and water were removed.

The product was dissolved in 100 ml of water and 58.9 g (0.52 mole) of 30% hydrogen peroxide was added thereto dropwise while the temperature was kept at 60° to 70° C., then it was matured at 90° C. for 1 hour. The solvent and the like was removed from the reaction mixture by evaporator to give 147.1 g (0.44 mole) of a colorless, transparent and viscous liquid.

The product was identified as bis-(2-carboxypropyl)-1,1,3,3-tetramethylbutylphosphine oxide by analysis with FAB-MASS, $^1$H-NMR and FT-IR.

FAB-MASS: m/z=335[M+H]$^+$ $^1$H-NMR (CDCl$_3$, δ): 1.05 (s, 9H), 1.32 (d, 6H, J=16.7 Hz), 1.34 (d, 3H, J=7.14 Hz), 1.67 (d, 2H, J=15.5 Hz), 2.11 (m, $^1$H), 2.94 (m, 2H), 8.70 (s, 2H).

The results of FT-IR analysis are shown in Table 1.

Example 5

A 500 ml pressure resistant glass vessel equipped with a thermometer, a stirrer and a pressure gauge was sufficiently purged with nitrogen. To the vessel which was kept under reduced pressure, were added 45.1 g (0.5 mole) of tert-butylphosphine and 70.5 g (0.75 mole) of concentrated hydrochloric acid. While stirring the mixture, 72.1 g (1.0 mole) of acrylic acid was added thereto by a pressure pump while the temperature was kept at 30° C. or less, and reaction was further carried out at room temperature for 1 hour. The reaction mixture removed under a nitrogen atmosphere was a homogeneous, colorless and transparent liquid. The liquid was concentrated by an evaporator to remove the excess hydrochloric acid and water.

The resulting product was dissolved in 100 ml of water and 58.9 g (0.52 mole) of 30% hydrogen peroxide was added thereto dropwise while the temperature was kept at 60° to 70° C. The mixture was then matured at 90° C. for 1 hour. The liquid was concentrated until it reached one-half of its original volume and then the precipitated crystal was filtered out and washed with water, dried in vacuum to give 107.6 g (0.43 mole) of a white crystal having a melting point of 188° C.

The product was identified as bis(2-carboxyethyl)-tert-butylphosphine oxide by analysis with FAB-MASS, $^1$H-NMR, and FT-IR.

FAB-MASS: m/z=251 [M+H]$^+$ $^1$H-NMR (CDCl$_3$, δ): 1.15 (s, 9H, J=14.3 Hz), 2.32 (m, 4H), 2.82 (m, 4H), 8.42 (s, 2H).

The results of FT-IR analysis are shown in Table 1.

Example 6

A pressure resistant glass vessel analogous to that of Example 5 was used and 45.1 g (0.5 mole) of tert-butylphosphine and 70.5 g (0.75 mole) of concentrated hydrochloric acid were charged therein. While stirring the mixture, 100.1 g (1.0 mole) of ethyl acrylate was added thereto by a pressure pump while the temperature was kept at 30° C. or less, and reaction was further carried out at room temperature for 20 hours. The reaction mixture removed under a nitrogen atmosphere was a homogeneous, colorless and transparent liquid. The liquid was concentrated by an evaporator to remove the excess hydrochloric acid and water.

The resulting product was dissolved in 100 ml of ethanol and 58.9 g (0.52 mole) of 30% hydrogen peroxide was added thereto dropwise while the temperature was kept at 60° to 70° C. After completion of the dropping, the mixture was matured at 90° C. for 1 hour. The solvent and the like were removed by evaporator from the reaction mixture to give 119.4 g (0.39 mole) of a colorless, transparent and viscous liquid.

The product was identified as bis(2-carbethoxyethyl)-tert-butylphosphine oxide by analysis with FAB-MASS, $^1$H-NMR, and FT-IR.

FAB-MASS: m/z=307 [M+H]$^+$ $^1$H-NMR (CDCl$_3$, δ): 1.15 (d, 9H, J=14.2 Hz) , 1.29 (t, 6H, J=7.45 Hz), 2.30 (m, 4H), 2.75 (m, 4H), 4.20 (q, 4H, J=7.14 Hz) .

The results of FT-IR analysis are shown in Table 1.

Example 7

A pressure resistant glass vessel analogous to that of Example 5 was used and 45.1 g (0.5 mole) of tert-butylphosphine and 70.5 g (0.75 mole) of concentrated hydrochloric acid were charged therein. While stirring the mixture, 116.1 g (1.0 mole) of acrylic acid 2-hydroxyethyl ester was added thereto by a pressure pump while the temperature was kept at 30° C. or less, and reaction was further carried out at room temperature for 10 hours. The reaction mixture removed under a nitrogen atmosphere was a homogeneous, colorless and transparent liquid. The liquid was concentrated by an evaporator to remove the excess hydrochloric acid and water.

The resulting product was dissolved in 100 ml of water and 58.9 g (0.52 mole) of 30% hydrogen peroxide was added thereto dropwise while the temperature was kept at room temperature. The solvent and the like was removed from the reaction mixture by an evaporator to give 135.4 g (0.40 mole) of a colorless, transparent and viscous liquid.

The product was identified as bis[2-carbo(2-hydroxyethoxy) ethyl]-tert-butylphosphine oxide by analysis with FAB-MASS, $^1$H-NMR, and FT-IR.

FAB-MASS: m/z=339[M+H]$^+$ $^1$H-NMR (CDCl$_3$, δ): 1.13 (d, 9H, J=14.3 Hz), 2.30 (m, 4H), 2.83 (m, 4H), 3.72 (s, 2H), 3.75 (m, 4H), 4.32 (m, 4H).

The results of FT-IR analysis are shown in Table 1.

Example 8

A pressure resistant glass vessel analogous to that of Example 5 was used and 45.1 g (0.5 mole) of tert-butylphosphine and 70.5 g (0.75 mole) of concentrated hydrochloric acid were charged therein. While stirring the mixture, 86.1 g (1.0 mole) of methacrylic acid was added thereto by a pressure pump while the temperature was kept at 30° C. or less, and reaction was further carried out at room temperature for 5 hours. The reaction mixture removed under a nitrogen atmosphere was a homogeneous, colorless and transparent liquid. The liquid was concentrated by evaporator to remove the excess hydrochloric acid and water.

The resulting product was dissolved in 100 ml of water and 58.9 g (0.52 mole) of 30% hydrogen peroxide was added thereto dropwise while the temperature was kept at 60° to 70° C., then it was further matured at 90° C. for 1 hour. The solvent and the like were removed from the reaction mixture by evaporator to give 125.3 g (0.45 mole) of a colorless, transparent and viscous liquid.

The product was identified as bis(2-carboxypropyl)-tert-butylphosphine oxide by analysis with FAB-MASS, $^1$H-NMR, and FT-IR. The results of FT-IR analysis are shown in Table 1.

FAB-MASS: m/z=279[M+H]$^+$ $^1$H-NMR (CDCl$_3$, δ): 1.13 (d, 9H, J=14.0 Hz), 1.32 (d, 3H, J=7.10 Hz), 2.15 (m, 1H), 2.92 (m, 2H), 8.50 (m, 2H).

FT-IR: (shown in Table 1)

Comparative Example 1

A 500 ml four-necked flask equipped with a condenser, a thermometer, and a stirrer was sufficiently purged with nitrogen, and 3.1 g (0.5 mole) of 1,1,3,3-tetramethylbutyl-phosphine and 100 ml of acetonitrile were chafed therein but they were not mixed, nor dissolved but rather were separated into two layers. While stirring the mixture, 15 ml of a 10 N aqueous potassium hydroxide solution was added thereto dropwise at a temperature of 20° C. or less. The mixture was cooled with ice to keep the temperature at 20° C. or less, and 106.1 g (1.0 mole) of acrylonitrile was added thereto gradually dropwise. By adding the acrylonitrile, that a large amount of phosphine gas distilled out from the top of the condenser was confirmed with filter paper impregnated with a silver nitrate solution which turned black. After completion of the reaction, a reddish yellow viscous liquid was obtained at the bottom of the flask, however, generation of the desired product, bis(2-cyanoethyl)-1,1,3,3-tetramethylbutylphosphine, was not recognized and the 1,1,3,3-tetramethylbutylphosphine decomposed easily in an alkali to become phosphine gas.

TABLE 1

| | FT-IR | | | | | | | |
|---|---|---|---|---|---|---|---|---|
| | Examples | | | | | | | |
| | 1 | 2 | 3 | 4 | 5 | 6 | 7 | 8 |
| free-OH stretching | | | 3400 | | | | 3400 | |
| —CH$_3$,C—H stretching | 2940 | 2970 | 2970 | 2970 | 2950 | 2980 | 2980 | 2970 |
| C=O stretching | 1722 | 1730 | 1730 | 1725 | 1725 | 1730 | 1730 | 1725 |
| —CH$_3$,C—H asymmetric bending | 1472 | 1480 | 1475 | 1465 | 1480 | 1482 | 1475 | 1470 |
| —C—O stretching, and —OH bending | 1420 | | | | 1400 | 1418 | | 1405 |
| —CH$_3$,C—H symmetric bending | 1360 | 1370 | 1375 | 1370 | 1370 | 1380 | 1375 | 1370 |
| —C—O stretching, and —OH bending | 1255 | | | 1240 | 1245 | | | 1240 |
| P=O stretching | 1142 | 1155 | 1180 | 1160 | 1182 | 1180 | 1190 | 1180 |

What is claimed is:

1. A bifunctional alkyl phosphine oxide represented by the following general formula (1):

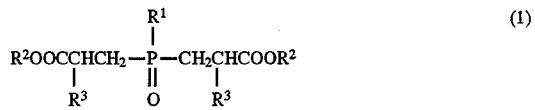

wherein R$^1$ is 1,1,3,3-tetramethylbutyl, R$^2$ represents a hydrogen atom, an alkyl group, or a hydroxyalkyl group having 1 to 8 carbon atoms, and R$^3$ represents a hydrogen atom or a methyl group.

2. A method of producing a bifunctional alkyl phosphine oxide of the formula (1):

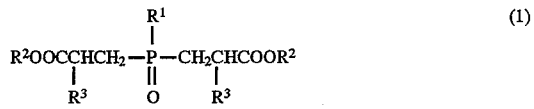

R$^1$ is an alkyl group represented by the following formula (2):

wherein n represents 0 or 1, R$^2$ represents a hydrogen atom, an alkyl group and a hydroxyalkyl group having 1 to 8 carbon atoms, and R$^3$ represents a hydrogen atom and a methyl group, which comprises:

reacting (meth)acrylic acid or an ester thereof of the formula (4):

wherein R$^2$ is hydrogen, alkyl or a hydroxyalkyl group of 1 to 8 carbon atoms, and R$^3$ is hydrogen or methyl with a monoalkyl phosphine of formula (3):

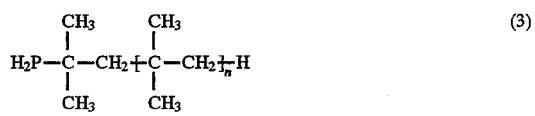

wherein n is 0 or 1 in the presence of an acid catalyst; and oxidizing the compound produced in the first step to the bifunctional alkylphosphine oxide of formula (1) with an oxidizing agent.

3. The method of claim 2, wherein R$^1$ is 1,1,3,3-tetramethylbutyl.

4. The method of claim 2, wherein R$^1$ is a t-butyl group.

5. The method of claim 2, wherein said (meth)acrylic ester of formula (4) is methylacrylate, ethylacrylate, butylacrylate, 2-ethylhexylacrylate, methylmethacrylate, ethylmethacrylate, butylmethacrylate, 2-ethylhexylmethacrylate or 2-hydroxyethylacrylate.

6. The method of claim 2, wherein said acid catalyst is hydrochloric acid, sulfuric acid, nitric acid, phosphoric acid, perchloric acid, periodic acid, hydrofluoric acid or methanesulfonic acid.

7. The method of claim 2, wherein said oxidizing agent is hydrogen peroxide, benzoyl peroxide, nitric acid, nitrogen oxide or chlorine.

8. The method of claim 2, wherein the reaction temperature of the first step ranges from −30° to 30° C.

9. The method of claim 2, wherein from 2 to 5 mols of (meth)acrylic acid or ester thereof is reacted with 1 mol of monoalkylphosphine.

10. The method of claim 2, wherein, in the oxidation step, from 1.0 to 1.1 mols of oxidizing agent is reacted with the reaction product of the first step in terms of 1 mol of the initial monoalkylphosphine reactant.

11. The method of claim 2, wherein the reaction temperature of the oxidization reaction ranges from room temperature to 90° C.

* * * * *